United States Patent
Inoue et al.

(10) Patent No.: US 7,586,606 B2
(45) Date of Patent: Sep. 8, 2009

(54) NEAR-FIELD POLARIZED-LIGHT MEASUREMENT APPARATUS

(75) Inventors: Tsutomu Inoue, Hachioji (JP); Fuminori Sato, Hachioji (JP); Yoshihito Narita, Hachioji (JP); Mutsumi Senuma, Hachioji (JP)

(73) Assignee: JASCO Corporation, Hachioji-shi, Tokyo (JP)

( * ) Notice: Subject to any disclaimer, the term of this patent is extended or adjusted under 35 U.S.C. 154(b) by 47 days.

(21) Appl. No.: 11/398,096

(22) Filed: Apr. 5, 2006

(65) Prior Publication Data
US 2006/0238758 A1 Oct. 26, 2006

(30) Foreign Application Priority Data
Apr. 20, 2005 (JP) .............................. 2005-122311

(51) Int. Cl.
*G01J 4/00* (2006.01)
(52) U.S. Cl. ...................................... 356/364
(58) Field of Classification Search .......... 356/364–370
See application file for complete search history.

(56) References Cited

U.S. PATENT DOCUMENTS 5,581,532 A * 12/1996 Matsumura et al. ...... 369/13.31
6,046,448 A * 4/2000 Sato et al. ................... 250/234
2003/0184750 A1 * 10/2003 Aikens et al. ............... 356/369

FOREIGN PATENT DOCUMENTS

EP 0880043 A2 11/1998

OTHER PUBLICATIONS

Japanese Patent Abstract, Publication No. 55-103434, published Aug. 7, 1980, "Polarimeter," Application No. 54-010902, filed Feb. 1, 1979.
Japanese Patent Abstract, Publ. No. 2002-162333, published Jun 7, 2002, "Near Field Probe, Manufacturing Method Of Near Field Probe And Near Field Microscope Using Near Field Probe".
Inoue et al., "Near-field fiber probe for polarization spectroscopy," Vibrational Spectroscopy 35 (2004), pp. 33-37.
Betzig et al., "Polarization contrast in near-field scanning optical microscopy," Applied Optics, Aug. 1, 1992, vol. 31, No. 22, pp. 4563-4568.
European Search Report for EP06111974 dated Mar. 2, 2007, two pages.

* cited by examiner

*Primary Examiner*—Tarifur Chowdhury
*Assistant Examiner*—Tara S Pajoohi
(74) *Attorney, Agent, or Firm*—Rankin, Hill & Clark LLP

(57) ABSTRACT

A near-field polarized-light measurement apparatus 10 comprises a near-field probe 14, an analyzer 18, a detector 22, and an analyzer-rotating unit 20. The near-field probe 14 has at a tip thereof an opening smaller than the wavelength of light used for measurement and generates linearly polarized near-field light from the opening and irradiates a sample with the near-field light. The detector 22 detects light transmitted through the sample via the analyzer 18. The analyzer-rotating unit 20 rotates the analyzer 18 about an optical axis to vary the angle of a transmission axis thereof. And optical rotation of the sample is measured by rotating the analyzer 18 with the analyzer-rotating unit 20.

4 Claims, 4 Drawing Sheets

NEAR-FIELD POLARIZED-LIGHT MEASUREMENT APPARATUS

RELATED APPLICATIONS

This application claims priority to the Japanese Patent Application 2005-122311 dated on Apr. 20, 2005 and is hereby incorporated with reference for all purposes.

BACKGROUND OF THE INVENTION

1. Field of the Invention

The present invention relates to polarized-light measurement apparatuses for measuring optical rotation and optical rotatory dispersion, and in particular, to an improvement in the spatial resolution thereof.

2. Description of the Related Art

Many biological substances exhibit characteristics whereby the plane of polarization of linearly polarized light transmitted through the substance is rotated (this effect is known as optical activity). Measurement of the optical activity is carried out to analyze the three-dimensional structure of substances. Apparatuses used to measure the optical activity or the wavelength dependence thereof (called optical rotatory dispersion) are known as optical activity spectrometers or optical rotatory dispersion spectrometers, respectively (for example, see Japanese Unexamined Patent Application Publication No. S55-103434).

However, with the optical activity spectrometers and optical rotatory dispersion spectrometers mentioned above, similarly to standard optical measurement apparatuses, it is not possible to perform measurement at scales smaller than the wavelength of the light used for measurement. In other words, similarly to other optical measurement apparatuses, there is a limit to the spatial resolution due to the diffraction limit of light.

SUMMARY OF THE INVENTION

The present invention has been conceived in light of the problem described above, and an object thereof is to provide a near-field polarized-light measurement apparatus having a spatial resolution beyond the diffraction limit of light used for the measurement.

In order to realize the object described above, the present inventors, as a result of extensive investigation, have determined that it is most appropriate to employ a near-field technique to measure the optical rotation.

A near-field polarized-light measurement apparatus of the present invention comprises a near-field probe, an analyzer, a detector, and an analyzer-rotating unit. The near-field probe has at a tip thereof an opening smaller than the wavelength of light used for measurement and generates linearly polarized near-field light from the opening and irradiates a sample with the near-field light. The detector detects light transmitted through the sample via the analyzer. The analyzer-rotating unit rotates the analyzer about an optical axis to vary the angle of a transmission axis thereof. And optical rotation of the sample is measured by rotating the analyzer with the analyzer-rotating unit.

In the near-field polarized-light measurement apparatus according to the present invention, it is preferable that the apparatus further comprises a polarization modulator disposed before the analyzer. The polarization modulator varies the orientation of a plane of polarization of the linearly polarized light at a predetermined modulation frequency. Based on a frequency component corresponding to the modulation frequency of the polarization modulator and/or higher harmonic frequencies thereof in a detection signal from the detector, the transmission axis of the analyzer is rotated by the analyzer-rotating unit. And the optical rotation of the sample is measured from rotation angle information of the analyzer.

A near-field polarized-light measurement apparatus of the present invention comprises a light-radiating device, a polarizer disposed after the light-radiating device, a near-field probe, a light-collection-direction rotating unit, and a detector. The light-radiating device irradiates a sample with light. The polarizer converts the light irradiating the sample into linerly polarized light. The near-field probe has at a tip thereof an opening smaller than the wavelength of light used for measurement and collects the linearly polarized light transmitted through the sample from the opening. The light-collection-direction rotating unit changes the angle of the linearly polarized light collected at the near-field probe. The detector detects the light collected by the near-field probe.

In the near-field polarized-light measurement apparatus according to the present invention, it is preferable that the apparatus further comprises a polarization modulator disposed in an optical path between the polarizer and the detector. The polarization modulator changes the orientation of a plane of polarization of the linearly polarized light. Based on a frequency component corresponding to a modulation frequency of the polarization modulator and/or higher harmonic frequencies thereof in a detection signal from the detector, the angle of the linearly polarized light collected at the near-field probe is changed by the light-collection-direction rotating unit. And the optical rotation of the sample is measured from rotation angle information.

In the near-field polarized-light measurement apparatus according to the present invention, it is preferable that the polarization modulator is formed of a Faraday cell.

In the near-field polarized-light measurement apparatus according to the present invention, it is preferable that the near-field probe selectively generates or collects linearly polarized light.

In the near-field polarized-light measurement apparatus according to the present invention, it is preferable that the opening in the near-field probe is elliptical or slit-shaped.

In the near-field polarized-light measurement apparatus according to the present invention, it is preferable that the apparatus further comprises a spectroscope for splitting the light irradiating the sample or the light detected at the detector into spectral components. The optical rotatory dispersion of the sample is measured with the apparatus.

In the near-field polarized-light measurement apparatus according to the present invention, it is preferable that the apparatus further comprises a moving mechanism for moving the position of the tip of the near-field probe relative to a measurement surface of the sample in X and Y directions orthogonal to a normal thereof. Mapping measurement is performed for the measurement surface of the sample with the apparatus.

With a near-field polarized-light measurement apparatus according to the present invention, because the optical rotation of a sample is measured using a near-field probe, it is possible to perform measurement with extremely high spatial resolution.

DESCRIPTION OF THE PREFERRED EMBODIMENT

Figure 1A:
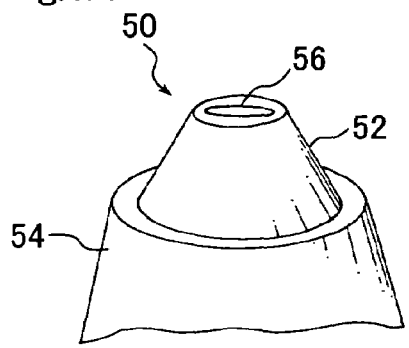
FIGS. 1A and 1B are outlined diagrams showing the structure of a polarized-light near-field probe.
Figure 1B:
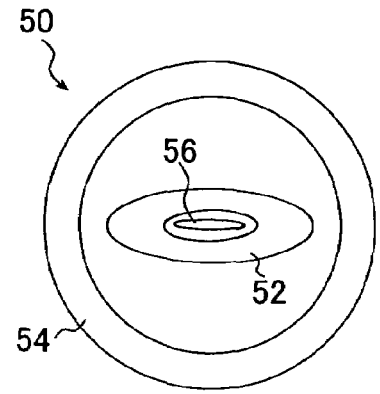
Figure 2:
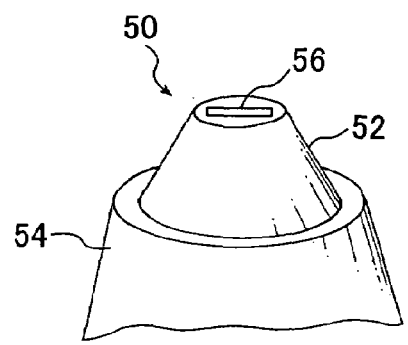
FIG. 2 is an outlined diagram showing another design of the polarized-light near-field probe.

First, in order to ascertain whether it was possible to measure optical rotation using near-field light, the inventors conducted experiments to investigate the polarized-light transfer characteristics of a near-field probe. The probe used in these experiments had an elliptical or slit-shaped opening, as shown in FIGS. 1A and 1B or FIG. 2, respectively. (See Japanese Unexamined Patent Application Publication No. 2002-162333.) FIG. 1A is a magnified perspective view of a vicinity of the tip of a near-field probe 50 having an elliptical opening, and FIG. 1B is a top view thereof. FIG. 2 is a perspective view of the near-field probe 50 when it has a slit-shaped opening. The near field-probe 50 shown in FIGS. 1A, 1B, and 2 is constituted by a pointed portion 52 which is formed by tapering the end of an optical fiber having an elliptical or slit-shaped core in a substantially conical shape. A gold (Au) thin film is formed on the surface of the near-field probe 50 to serve as a mask 54. An elliptical or slit-shaped opening 56 for obtaining linearly polarized light in a predetermined oscillation direction is formed at the extreme tip of the substantially conical tapered portion 52. With this structure, the near-field probe 50 in FIGS. 1A, 1B, and 2 can selectively emit or collect linearly polarized light that is polarized in a predetermined direction (orthogonal to the longitudinal direction of the opening 56).

Figure 3:
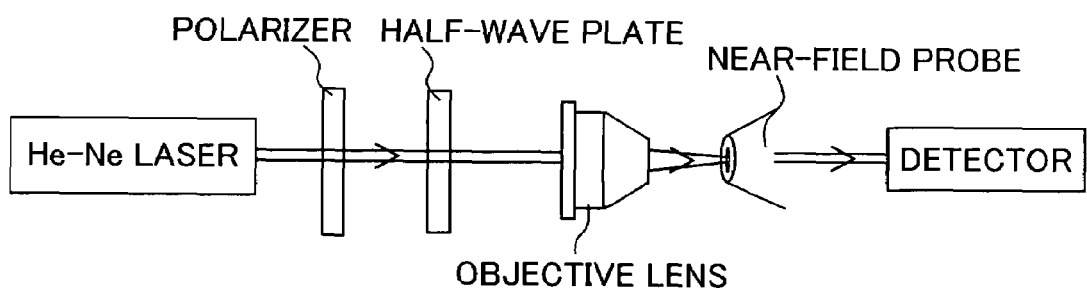
FIG. 3 is a diagram of an apparatus used in experiments for obtaining the polarization characteristics of the near-field probe.
Figure 4:
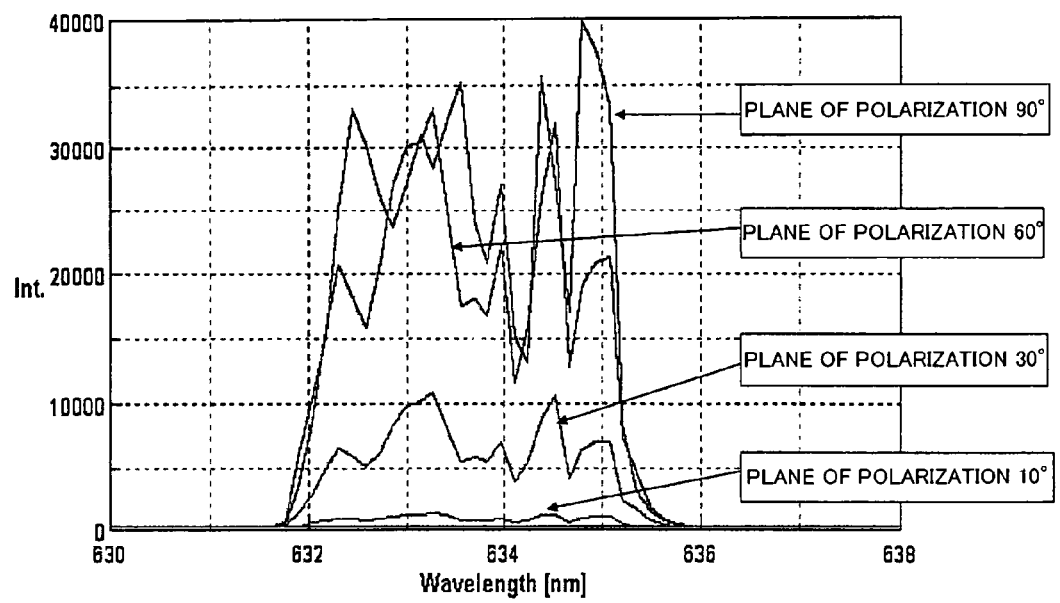
FIG. 4 is a graph showing results of the polarization characteristics experiments.
Figure 5A:
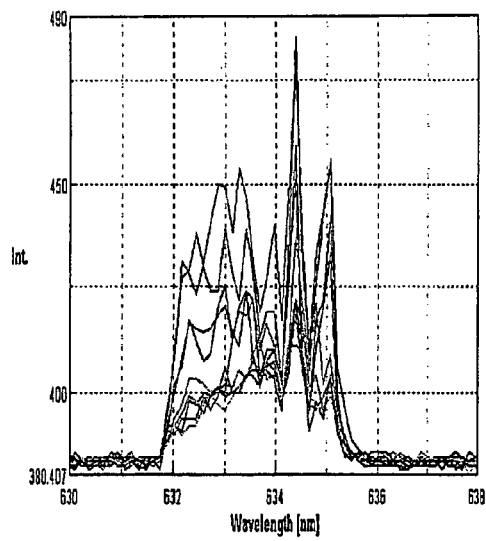
FIGS. 5A and 5B are graphs showing results of the polarization characteristics experiments.
Figure 5B:
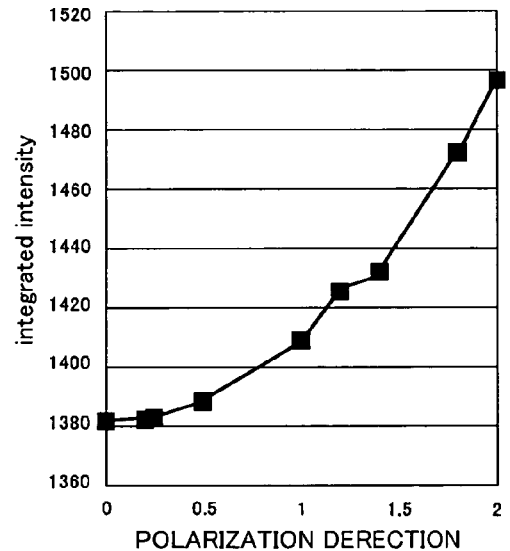

FIG. 3 shows the configuration of an apparatus used in the experiments. In the apparatus in FIG. 3, laser light from a He-Ne laser passes through a polarizer, a half-wave plate, and an objective lens and irradiates the opening of the near-field probe described above, and the light collected at the opening is detected with a detector. The near-field probe used in the experiments has an elliptical opening with a short axis of 50 nm and a long axis of 500 nm (see FIGS. 1A and 1B). The half-wave plate was rotated about the optical axis to vary the angle of the plane of polarization with respect to the long axis of the opening in the near-field probe, and the collection efficiency at that time was measured. FIG. 4 shows spectra of the light collected by the probe when the plane of polarization was rotated by 10°, 30°, 60°, and 90°. FIGS. 5A and 5B respectively show spectra and integrated intensity when the plane of polarization was varied from 0° to 2°. It is evident from these figures that the near-field probe has good polarization selectivity. In other words, it is clear that superior optical rotation measurement can be accomplished using the near-field probe described above, even for near-field light.

Furthermore, an experiment was also carried out using the near-field probe in a light-emitting mode, and good polarization selectivity was obtained in this case too.

The present invention has been conceived in light of the findings described above. Preferred embodiments will now be described below with reference to the drawings.

Figure 6:
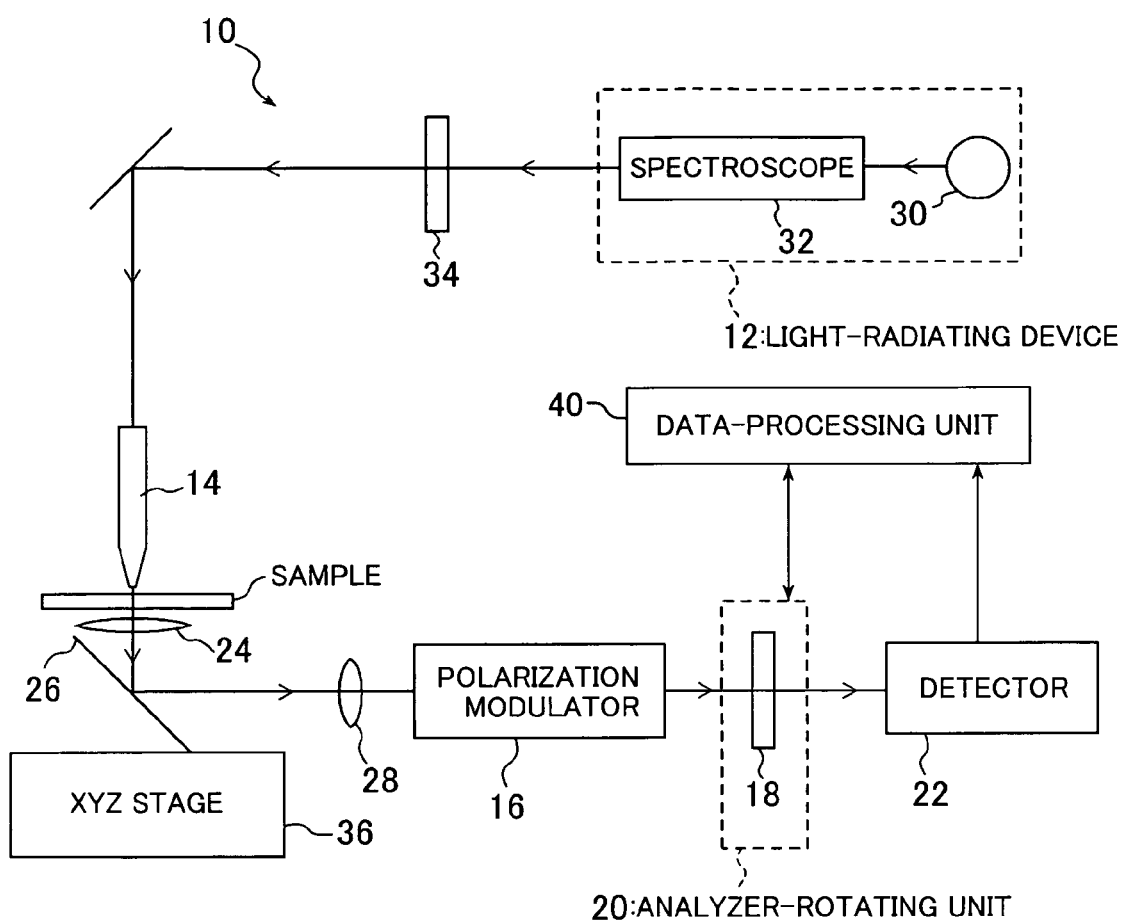
FIG. 6 is an outlined diagram showing the structure of a near-field polarized-light measurement apparatus (light-emitting type) according to a first embodiment of the present invention.

FIG. 6 is an outlined diagram showing the configuration of a near-field polarized-light measurement apparatus 10 according to a first embodiment of the present invention. The near-field polarized-light measurement apparatus 10 includes a light-radiating device 12, a near-field probe 14, a polarization modulator 16, an analyzer 18, an analyzer-rotating unit 20, and a detector 22. Linearly polarized light emitted from the light-radiating device 12 enters the near-field probe 14 from an entrance end and is guided inside the near-field probe 14. The light guided in the near-field probe 14 generates near-field light at the opening in the tip of the probe 14. This linearly polarized near-field light then irradiates a sample. The linearly polarized light that passes through the sample is collected by an objective lens 24, is reflected at a mirror 26 such as dichroic mirror, passes through a lens 28, and reaches the polarization modulator 16. Linearly polarized, whose plane of polarization is modulated at a predetermined modulation frequency upon transmission through the polarization modulator 16, passes through the analyzer 18 and is detected at the detector 22. The analyzer 18 is configured so that the transmission axis thereof can be rotated on the optical axis using the analyzer-rotating unit 20.

The light-radiating device 12 is formed of a light source 30 and a spectroscope 32. Light from the light source 30 is divided into spectral components by the spectroscope 32, and wavelength scanning is performed to measure the spectral dependency of the optical rotation (optical rotatory dispersion). A polarizer 34 is disposed after the light-radiating device 12 to linearly polarize the light to be guided in the near-field probe 14. The present embodiment is illustrated by an example where the spectroscope 32 is placed at the light-emission side, but it may be placed at the detector 22 side so that only light of predetermined wavelengths in the light transmitted through the sample is detected at the detector 22.

A polarized-light probe having an elliptical or slit-shaped opening, as shown in FIGS. 1A and 1B or FIG. 2, is used as the near-field probe 14 in the present embodiment (see Japanese Unexamined Patent Application Publication No. 2002-162333). Although in the example shown here, a near-field probe that selectively generates linearly polarized light is used, the present invention is not limited to this; a near-field probe with a different structure may be used. For example, a standard near-field probe, that is, a near-field probe that generates near-field light without affecting the polarization state of the guided light, may be used. In such a case, a configuration in which light from the light-radiating device 12 passes through the polarizer 34 and is guided in the probe 14 may be used. However, in a standard optical-fiber-based probe, the polarization state of laser light is destroyed due to changes in the optical fiber curvature, length, and so on, and therefore, it is preferable to use a polarized-light probe, such as that described in the present embodiment.

The polarization modulator 16 is formed of a modulator such as a Faraday cell, an oscillator for oscillating the Faraday cell at a predetermined modulation frequency, and so on. The polarization modulator 16 thus oscillates the orientation of the plane of polarization of the linearly polarized light at a predetermined modulation frequency.

The analyzer-rotating unit 20 is formed of a gear, a servo motor, and so forth, and rotates the analyzer 18 about the optical axis to vary the direction of the transmission axis thereof. The amount of rotation of the analyzer 18 is sent to a data-processing unit 40.

The light transmitted through the analyzer 18 is detected in the detector 22, and a detection signal therefrom is sent to the data-processing unit 40. Measurement of the optical rotation of the sample is performed in the data-processing unit 40 based on the detection signal from the detector 22 by rotating the analyzer 18.

Furthermore, the near-field polarized-light measurement apparatus 10 according to the present embodiment also includes an XYZ stage 36 (moving mechanism) for controlling the positional relationship of the sample and the probe 14. The sample, the objective lens 24, and the mirror 26 are mounted on the XYZ stage 36, and the XYZ stage 36 moves these components in the horizontal directions (X and Y directions) and the vertical direction (Z direction). Accordingly, by moving the position of the tip of the near-field probe 14 relative to the measurement surface of the sample, in the X and Y directions orthogonal to the normal thereof, to change the measurement position on the sample surface, it is possible to perform mapping measurement of the optical rotation and optical rotatory dispersion.

Measurement of the optical rotation is carried out as follows. First, in the absence of the sample, the direction of the transmission axis of the analyzer 18 is adjusted using the analyzer-rotating unit 20 so that the transmission axes of the polarizer and the analyzer are perpendicular to each other, in other words, so that the detected light is minimized. Then, after inserting the sample, it is irradiated with linearly polarized near-field light from the near-field probe 14. The light transmitted through the sample is collected by the objective lens 24 and is directed to the polarization modulator 16. Light whose polarization is modulated at the predetermined modulation frequency by the polarization modulator 16 then passes through the analyzer 18 and is detected at the detector 22. The data-processing unit 40 then rotates the transmission axis of the analyzer 18 using the analyzer-rotating unit 20 so that, in the detection signal from the detector 22, a frequency component equal to the modulation frequency of the polarization modulator 16 is eliminated. The rotation angle is measured from the angle of the transmission axis at that point.

According to the near-field polarized-light measurement apparatus 10 of the present embodiment, as described above, because the optical rotation or optical rotatory dispersion of the sample is measured using a near-field optical technique, it is possible to measure the optical rotation or optical rotatory dispersion with a spatial resolution surpassing the diffraction limit of light.

Also, the present embodiment is configured such that the polarization modulator 16 for oscillating the plane of polarization of the linearly polarized light at the predetermined frequency is provided in the optical path between the light-radiating device 12 and the detector 22, and the optical rotation or optical rotatory dispersion of the sample is measured with symmetric angular oscillation method using the optical-null principle. With this method, it is possible to attain a resolution of ±0.1 degree when measuring the optical rotation.

In the embodiment described above, the polarization modulator 16 is disposed in the optical path, and the optical rotation or optical rotatory dispersion of the sample is measured with symmetric angular oscillation method using the optical-null principle; however, instead of providing the polarization modulator 16, a configuration in which the optical rotation or optical rotatory dispersion is measured from the rotation angle of the analyzer 18 is also possible (the crossed-Nicol method). More specifically, the optical rotation may be obtained by the following procedure: First a reference configuration is determined; in this configuration, the transmission axes of the polarizer 34 and analyzer 18 are positioned so that, in the absence of the sample, the detected light level is minimized. Then, with the sample in place, the optical rotation is determined from the rotation angle of the analyzer 18 where the detected light level is minimized. Alternatively, the analyzer 18 may be rotated or oscillated to determine the optical rotation from the detection signal component corresponding to double the frequency of the angular frequency thereof. However, in view of the measurement precision, it is preferable to employ the symmetric angle-oscillating method, as in the embodiment described above. The measurement precision of the crossed-Nicol method is generally about ±0.5 degree, whereas a measurement precision as high as ±0.1 degree can be attained with the embodiment described above.

Figure 7:
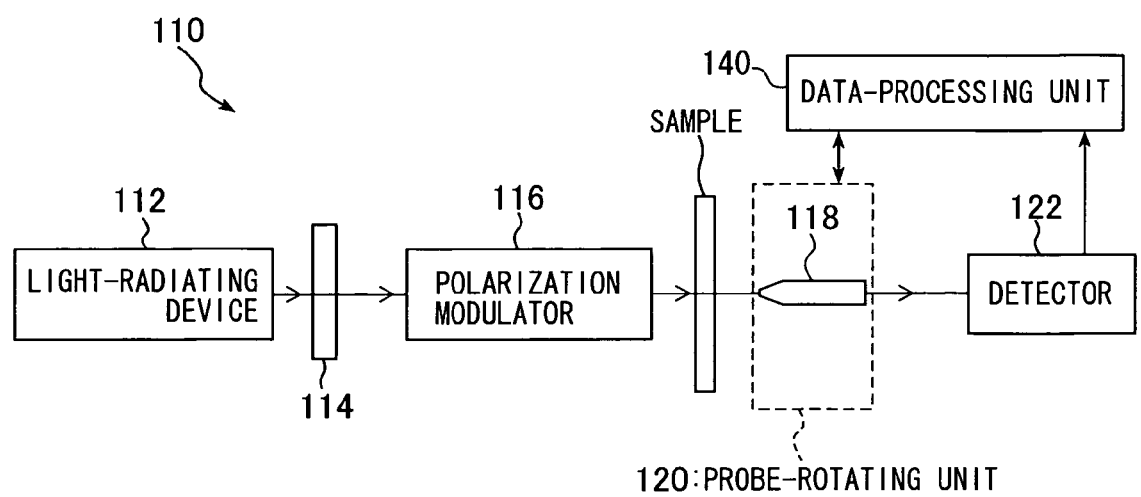
FIG. 7 is a diagram showing the structure of a near-field polarized-light measurement apparatus (light-collecting type) according to a second embodiment of the present invention.

The first embodiment is illustrated by using the near-field probe to radiate light; however, the apparatus may be configured using a near-field probe to collect light. FIG. 7 is a diagram of a second embodiment in which a near-field probe is used to collect light.

A near-field polarized-light measurement apparatus 110 in FIG. 7 includes a light-radiating device 112 for irradiating a sample with light; a polarizer 114, disposed after the light-radiating device 112, for linearly polarizing the light irradiating the sample; a polarization modulator 116, disposed after the polarizer 114, for changing the orientation of the plane of polarization of the linearly polarized light; a near-field probe 118 for collecting the linearly polarized light transmitted through the sample; a probe-rotating unit 120 (light-collection-direction rotating unit) for rotating the near-field probe 118 about the optical axis to change the angle of a transmission axis thereof; and a detector 112 for detecting the light collected by the near-field probe 118. Also in this embodiment, a probe having an elliptical or slit-shaped opening, as shown in FIGS. 1A and 1B or FIG. 2, is used as the near-field probe 118.

The light emitted from the light-radiating device 112 becomes linearly polarized light having a plane of polarization in a predetermined direction upon passing through the polarizer 114. The plane of polarization of this linearly polarized light is modulated at a predetermined frequency by the polarization modulator 116, and the modulated linearly polarized light is collected by a collecting lens or the like (not shown) and irradiates the sample. The light transmitted through the sample is collected by the near-field probe 118 and is detected at the detector 122. The detected data is then sent to a data-processing unit 140. The near-field probe 118 selectively collects linearly polarized light in a predetermined direction and functions as the analyzer shown in the embodiment in FIG. 6. To do so, the probe-rotating unit 120 is provided as a light-collection-direction rotating unit for varying the angle of the linearly polarized light collected at the near-field probe 118. Information about the angle of orientation of the collected linearly polarized light is also sent to the data-processing unit 140. Other possible forms of the light-collection-direction rotating unit include a configuration in which light from the sample is collected with the near-field probe after passing through an analyzer and the analyzer is rotated about the optical axis.

Measurement of the optical rotation of the sample is performed in the same way as in the embodiment shown in FIG. 6. First, in the absence of the sample, the orientation of the transmission axis of the near-field probe 118 is adjusted by the probe-rotating unit 120 so that the transmission axis of the polarizer 114 and the transmission axis of the near-field probe 118 are orthogonal, in order to minimize the level of light detected. In the present embodiment, a probe having an elliptical or slit-shaped opening is used as the near-field probe 118; a direction orthogonal to the longitudinal direction of this opening is the transmission-axis direction of the probe, and linearly polarized light in this transmission-axis direction is selectively collected. Thus, the transmission-axis direction is varied by rotating the near-field probe 118 about the optical axis using the probe-rotating unit 120. Then, the sample is put in place and light transmitting through the sample is collected by the near-field probe 118. The data-processing unit 140 rotates the transmission axis of the near-field probe 118 (the direction of the short-axis of the opening) by means of the probe-rotating unit 120 so that, in a detection signal from the detector 122, a frequency component equal to the modulation frequency of the polarization modulator 116 is eliminated. The rotation angle is measured from the angle of the transmission axis at that point.

In this way, it is also possible to perform superior optical rotation measurement when a near-field probe is used in the light-collecting mode. Furthermore, because the transmission efficiency of a near-field probe having an opening is generally low, there is a risk of the light not reaching the detector when using a sample having poor transmittance in the light-radiating mode. However, because the sample can be strongly irradiated with light using the configuration in the second embodiment, it is possible to perform satisfactory measurement, even of a sample having poor transmittance.

In the first and second embodiments described above, a polarized-light probe having a slit-shaped or elliptical opening was used (see FIGS. 1A and 1B or FIG. 2). By using such a polarized-light probe, it is possible to stably emit and detect a linearly polarized light. However, in a standard optical-fiber-based probe, the polarization state of laser light is destroyed due to changes in the fiber curvature, length, and so forth, and therefore, it is not possible to utilize the coherence characteristics of the laser light. Furthermore, although the detection sensitivity increases as the near-field light emitted from a minute aperture becomes more linearly polarized, in a standard probe, the near-field light becomes elliptically polarized, and the sensitivity thus decreases. In contrast, when using a polarized-light probe like that in the present invention, the polarization state of the laser light is not destroyed, and it is thus possible to emit and detect near-field light with a stable polarization state.

What is claimed is:

1. A near-field polarized-light measurement apparatus comprising:
    a light-radiating device for irradiating a sample with light;
    a polarizer disposed after the light-radiating device, for linearly polarizing the light irradiating the sample;
    a near-field probe having at a tip thereof an opening smaller than the wavelength of light used for measurement, wherein the opening in the near-field probe is elliptical or slit-shaped, for selectively collecting the linearly polarized light transmitted through the sample to the opening;
    a light-collection-direction rotating unit for changing the angle of the linearly polarized light collected at the near-field probe by rotating the near-field probe about the optical axis to change the angle of a transmission axis thereof; and
    a detector for detecting the light collected by the near-field probe,
    a polarization modulator disposed in an optical path between the polarizer and the detector, for changing the orientation of a plane of polarization of the linearly polarized light,
    wherein, based on a frequency component corresponding to a modulation frequency of the polarization modulator and/or higher harmonic frequencies thereof in a detection signal from the detector, the angle of the linearly polarized light collected at the near-field probe is changed by the light-collection-direction rotating unit, and the optical rotation of the sample is measured by symmetric angular oscillation using the optical-null principle.

2. The near-field polarized-light measurement apparatus of claim 1, wherein the polarization modulator is formed of a Faraday cell.

3. The near-field polarized-light measurement apparatus of claim 1, further comprising:
    a spectroscope for spliffing the light irradiating the sample or the light detected at the detector into spectral components,
    wherein the optical rotatory dispersion of the sample is measured.

4. The near-field polarized-light measurement apparatus of claim 1, further comprising:
    a moving mechanism for moving the position of the tip of the near-field probe relative to a measurement surface of the sample in X and Y directions orthogonal to a normal thereof, wherein mapping measurement is performed for the measurement surface of the sample.

* * * * *

UNITED STATES PATENT AND TRADEMARK OFFICE
CERTIFICATE OF CORRECTION

PATENT NO. : 7,586,606 B2
APPLICATION NO. : 11/398096
DATED : September 8, 2009
INVENTOR(S) : Tsutomu Inoue et al.

It is certified that error appears in the above-identified patent and that said Letters Patent is hereby corrected as shown below:

In the claims, column 8, line 34, that portion of the claim reading "a spectroscope for spliffing the light" should read -- a spectroscope for splitting the light --.

Signed and Sealed this

Twenty-seventh Day of July, 2010

David J. Kappos
*Director of the United States Patent and Trademark Office*